(12) United States Patent
Ikehara

(10) Patent No.: US 10,413,619 B2
(45) Date of Patent: Sep. 17, 2019

(54) IMAGING DEVICE

(71) Applicant: SHIMADZU CORPORATION, Kyoto-shi, Kyoto (JP)

(72) Inventor: Tatsuya Ikehara, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 431 days.

(21) Appl. No.: 15/157,907

(22) Filed: May 18, 2016

(65) Prior Publication Data

US 2016/0338593 A1 Nov. 24, 2016

(30) Foreign Application Priority Data

May 19, 2015 (JP) ................. 2015-101948

(51) Int. Cl.
*A61B 5/00* (2006.01)
*A61K 49/00* (2006.01)

(52) U.S. Cl.
CPC ...... *A61K 49/0021* (2013.01); *A61K 49/0034* (2013.01)

(58) Field of Classification Search
USPC ....................................... 600/431
See application file for complete search history.

(56) References Cited

U.S. PATENT DOCUMENTS

| | | |
|---|---|---|
| 2009/0285760 A1 | 11/2009 | Ishikawa et al. |
| 2012/0041305 A1* | 2/2012 | Grissom ............... A61B 5/415 |
| | | 600/431 |
| 2014/0254953 A1 | 9/2014 | Sato |
| 2014/0378843 A1* | 12/2014 | Valdes .................. G02B 21/06 |
| | | 600/476 |
| 2015/0030542 A1* | 1/2015 | Singhal ............. A61K 49/0034 |
| | | 424/9.6 |

FOREIGN PATENT DOCUMENTS

| | | |
|---|---|---|
| JP | 2006509573 A | 3/2006 |
| JP | 2006122234 A | 5/2006 |
| JP | 5110702 B2 | 12/2012 |
| JP | 5798430 B2 | 10/2015 |
| WO | 2009119369 A1 | 10/2009 |
| WO | 2009/139466 A1 | 11/2009 |

OTHER PUBLICATIONS

Communication dated May 22, 2018, from the Japanese Patent Office in counterpart application No. 2015-101948.

* cited by examiner

*Primary Examiner* — Nicole F Lavert
(74) *Attorney, Agent, or Firm* — Sughrue Mion, PLLC

(57) ABSTRACT

A first light source emits near-infrared radiation with a wavelength near 810 nm, which is excitation radiation for exciting indocyanine green, a second light source emits a violet light with a wavelength of 410 nm that is excitation radiation for exciting PpIX, and a third light source emits white light. An imaging portion comprises a first imaging element able to capture visible light, a second imaging element able to capture red light that is emitted by the PpIX, and a third imaging element able to capture near-infrared light emitted by the indocyanine green.

11 Claims, 13 Drawing Sheets

IMAGING DEVICE

TECHNICAL FIELD

The present invention relates to an imaging device that is used in, for example, in surgery on tumors, and, in particular, relates to an imaging device for capturing fluorescent light that is produced from a fluorescent dye through illumination, with excitation radiation, of a fluorescent dye that has been injected into a patient.

BACKGROUND ART

In recent years a technique known as near-infrared fluorescent imaging has been used in surgical procedures. In this near-infrared imaging, indocyanine green (ICG) has been injected, as a fluorescent dye into a tissue to be examined. Given this, when the indocyanine green is illuminated with near-infrared radiation of a wavelength of about 810 nm (nanometers), as excitation radiation, the indocyanine green emits near-infrared fluorescence at a wavelength of approximately 845 nm. This fluorescence is picked up by an imaging element that is able to detect near-infrared radiation, and an image thereof is displayed on a displaying portion such as a liquid crystal display panel, or the like. This near-infrared fluorescent imaging makes it possible to observe blood vessels, lymph ducts, and the like that exist to a depth of about 20 mm from the surface of the body.

This type of near-infrared fluorescent imaging is used in, for example, surgical procedures on tumors. For example, when performing a procedure for mammary cancer in surgery on a mammary gland, it is necessary to determine the position of the sentinel lymph node. This sentinel lymph node is the lymph node wherein the cancerous cells that are carried by the lymph flow first arrive. If no cancerous cells are discovered in the sentinel lymph node, then it can be concluded that the mammary cancer has not spread to the lymph nodes of the armpit region. The use of near-infrared fluorescent imaging in order to identify the location of the sentinel lymph node is effective for this purpose.

Moreover, in the same way, when carrying out a procedure for gastric cancer in abdominal surgery, the stage of cancer can be ascertained by the degree of spread to the lymph nodes in the region. Because the course of treatment will vary depending on the stage of cancer, it is possible to prevent overly aggressive treatment or insufficient treatment in advance through an evaluation of whether or not the cancer has spread to the lymph nodes in the region. Ascertaining the locations of the lymph nodes in the region through near-infrared fluorescent imaging is effective in this case as well.

Patent Document 1 discloses a data collecting method wherein an intensity distribution image of near-infrared fluorescence, obtained through exposing, to indocyanine green excitation radiation, an organ for in-vivo examination into which indocyanine green has been injected, with a carcinomatous lesion distribution image that has been obtained through the use of x-rays, nuclear magnetic resonance, or ultrasound on the organ prior to injection of the indocyanine green, to collect, as regional data for the tissue surrounding the cancer, data for regions that can be detected through the intensity distribution image of the near-infrared fluorescence but cannot be detected through the carcinomatous lesion distribution image.

PRIOR ART DOCUMENTS

Patent Documents

[Patent Document 1] International Patent Application Publication 2009/139466

SUMMARY OF THE INVENTION

Problem Solved by the Present Invention

While the near-infrared fluorescent imaging described above can be used to identify the locations of, for example, the necessary lymph nodes, it is not sufficient to enable an evaluation of a tumor, such as whether or not cancer has spread to a lymph node. Because of this, rapid diagnostics are required during surgery. The rapid diagnostics during surgery are performed through, for example, a pathological diagnostician, or the like, at the request of the surgeon, but this is limited to only large medical centers that have pathological diagnosticians as well. Because of this, there is a problem in that the near-infrared imaging cannot be used in hospitals that are unable to perform pathological diagnoses. Moreover, when these pathological diagnoses are performed, the diagnostic results must be provided immediately, so the overhead is large. In this way, it is a problem that performing near-infrared imaging alone does not make it possible to discern whether or not cancer has spread to the lymph node for which the location has been identified thereby.

On the other hand, techniques that use special fluorescent dies as fluorescent markers for tumors in surgical navigation have been of great interest in, primarily, neurosurgery. 5-ALA (5-aminolevulinic acid) has been used as such a fluorescent dye (a diagnostic agent used in fluorescent navigation). When this 5-aminolevulinic acid (hereinafter abbreviated "5-ALA") is used, the 5-ALA that is put into the body of the patient is converted into PpIX (protoporphyrin IX/protoporphyrin 9), which is a fluorescent substance. This PpIX has the property of accumulating specifically in tumors. Moreover, when visible light of a wavelength of approximately 410 nm is directed at the PpIX, which is the metabolite of 5-ALA, red visible light of a wavelength of approximately 630 nm is emitted by the PpIX. The spread of the cancer can be seen through observing the fluorescence from the PpIX. Note that PpIX is sometimes written as "Pp 9," instead.

The object of the present invention is to provide an imaging device wherein it is possible simultaneously to identify the locations of lymph nodes, and the like, and to identify tumors at those locations.

Means for Solving the Problem

A first invention is an imaging device wherein a first fluorescent dye that emits light through being illuminated with excitation radiation, and a second fluorescent dye that emits light through being illuminated with excitation radiation, and that has the nature of a metabolite thereof accumulating in a tumor, are placed in the body of a patient, and fluorescent light from the first fluorescent dye and fluorescent light from the second fluorescent dye are imaged, comprising: a first light source for emitting, toward the patient, light of a first wavelength for stimulating the first fluorescent dye; a second light source for emitting, toward the patient, light of a second wavelength for stimulating the second fluorescent dye; a third light source for emitting, toward the patient, a white light; a plurality of imaging elements; a filter for selectively causing first fluorescent light that is emitted by the first fluorescent dye, second fluorescent light that is emitted by the second fluorescent, and visible light that is reflected by the patient, to be incident into the plurality of imaging elements; and an image processing portion for displaying a first fluorescent image, a second fluorescent image, and a visible image on a displaying portion based on the first fluorescent light, the second fluorescent light, and the visible light captured by the plurality of imaging elements through the filter.

In a second invention, the image processing portion generates the second fluorescent image through taking a difference between the light of wavelengths corresponding to the second fluorescent light when the second light source is ON and the light of wavelengths corresponding to the second fluorescent light when the second light source is OFF.

In a third invention, the image processing portion comprises a correcting parameter processing portion for correcting the second fluorescent image through a correcting parameter that has been set in advance.

In a fourth invention, the first fluorescent dye, through being illuminated with the excitation radiation, emits infrared radiation as the fluorescent light, and the second fluorescent dye, through illumination with the excitation radiation, emits visible light as the fluorescent light; the plurality of imaging elements include a first imaging element able to capture visible light, a second imaging element able to capture the second fluorescent light that is emitted by the second fluorescent dye, and a third imaging element able to capture the first fluorescent light emitted by the first fluorescent dye; the filter includes a half-mirror for reflecting a portion of the visible light, reflected by the patient, to cause it to be incident into the first imaging element, and a dichroic mirror for passing the first fluorescent light that has passed through the aforementioned half-mirror to cause it to be incident into the third imaging element, and for reflecting the second fluorescent light, which has passed through the aforementioned half-mirror, to cause it to be incident into the second imaging element; the image processing portion includes a visible image processing portion for performing image processing on the visible light captured by the first imaging element to display it as a visible image on the displaying portion, a second fluorescent image processing portion for performing image processing on the second fluorescent light, captured by the second imaging element, to display it as a second fluorescent image on the displaying portion, and a first fluorescent image processing portion for performing image processing on the first fluorescent light, captured by the third imaging element, to display it as a first fluorescent image on the displaying portion; the visible image processing portion performs image processing on the visible light reflected from the patient when the third light source is ON to display it as a visible image on the displaying portion; the second fluorescent image processing portion performs image processing on the second fluorescent light that is emitted by the second fluorescent dye when the second light source is ON, to display it as a second fluorescent image on the displaying portion; and the first fluorescent image processing portion performs image processing on the first fluorescent light that is emitted by the first fluorescent dye when the first light source is ON, to display it as a first fluorescent image on the displaying portion.

In a fifth invention, the first fluorescent dye, through being illuminated with the excitation radiation, emits infrared radiation as the fluorescent light, and the second fluorescent dye, through illumination with the excitation radiation, emits visible light as the fluorescent light; the plurality of imaging elements include a first imaging element able to capture light of blue wavelengths, a second imaging element able to capture light of green wavelengths, and a third imaging element able to capture light of red wavelengths or longer; the filter includes a first dichroic mirror for reflecting light of a blue wavelengths, to cause it to be incident into the first imaging element, and a second dichroic mirror for passing light of a red wavelength or longer, which has passed through the first dichroic mirror, to cause it to be incident into the third imaging element, and for reflecting light of a green wavelength, which has passed through the first dichroic mirror, to cause it to be incident into the second imaging element; the image processing portion includes a visible image processing portion for performing image processing on the light captured by the first, second, and third imaging element to display it as a visible image on the displaying portion, a second fluorescent image processing portion for performing image processing on the second fluorescent light, captured by the third imaging element, to display it as a second fluorescent image on the displaying portion, and a first fluorescent image processing portion for performing image processing on the first fluorescent light, captured by the second imaging element, to display it as a first fluorescent image on the displaying portion; the visible image processing portion performs image processing on the visible light reflected from the patient when the third light source is ON to display it as a visible image on the displaying portion; the second fluorescent image processing portion performs image processing on the second fluorescent light that is emitted by the second fluorescent dye when the second light source is ON, to display it as a second fluorescent image on the displaying portion; and the first fluorescent image processing portion performs image processing on the first fluorescent light that is emitted by the first fluorescent dye when the first light source is ON, to display it as a first fluorescent image on the displaying portion.

In a sixth invention, the first fluorescent dye, through being illuminated with the excitation radiation, emits infrared radiation as the fluorescent light, and the second fluorescent dye, through illumination with the excitation radiation, emits visible light as the fluorescent light; the plurality of imaging elements includes a first imaging element that is able to capture visible light and a second imaging element that is able to capture infrared radiation; the filter includes a dichroic mirror that reflects the visible light, reflected from the patient, and the second fluorescent light that is emitted by the second fluorescent dye, and that passes the first fluorescent light that is emitted by the first fluorescent dye; the image processing portion includes a visible image processing portion for performing image processing on the visible light captured by the first imaging element to display it as a visible image on the displaying portion, a second fluorescent image processing portion for performing image processing on the second fluorescent light, captured by the first imaging element, to display it as a second fluorescent image on the displaying portion, and a first fluorescent image processing portion for performing image processing on the first fluorescent light, captured by the second imaging element, to display it as a first fluorescent image on the displaying portion; the visible image processing portion performs image processing on the visible light reflected from the patient when the third light source is ON to display it as a visible image on the displaying portion; the second fluorescent image processing portion performs image processing on the second fluorescent light that is emitted by the second fluorescent dye when the second light source is ON, to display it as a second fluorescent image on the displaying portion; and the first fluorescent image processing portion performs image processing on the first fluorescent light that is emitted by the first fluorescent dye when the first light source is ON, to display it as a first fluorescent image on the displaying portion.

A seventh invention comprises: an image compositing portion for compositing and displaying on to the displaying portion the first fluorescent image, the second fluorescent image, and the visible image.

In an eighth invention, the first fluorescent dye is indocyanine green, or the second fluorescent dye is 5-aminolevulinic acid.

Effects of the Invention

The first through eighth inventions enable identification of the location of lymph nodes, and the like, through the first fluorescent light, and also evaluation of a tumor through the second fluorescent light. That is, it is possible to use a simple device to identify the locations of lymph nodes, and the like, while simultaneously evaluating tumors in those locations.

The second invention makes it possible to prevent the effect of illumination of the room wherein the equipment is installed, enabling accurate measurement of the second fluorescent light from the second fluorescent dye.

The third invention enables an improvement in the accuracy of the evaluation of a tumor, through correcting the second fluorescent image through a correction parameter that has been set in advance.

The seventh invention enables easy specification of a correlation relationship through displaying the first fluorescent image, the second fluorescent image, and a visible image, composited on a displaying portion.

BRIEF DESCRIPTIONS OF THE DRAWINGS

Figure 5:
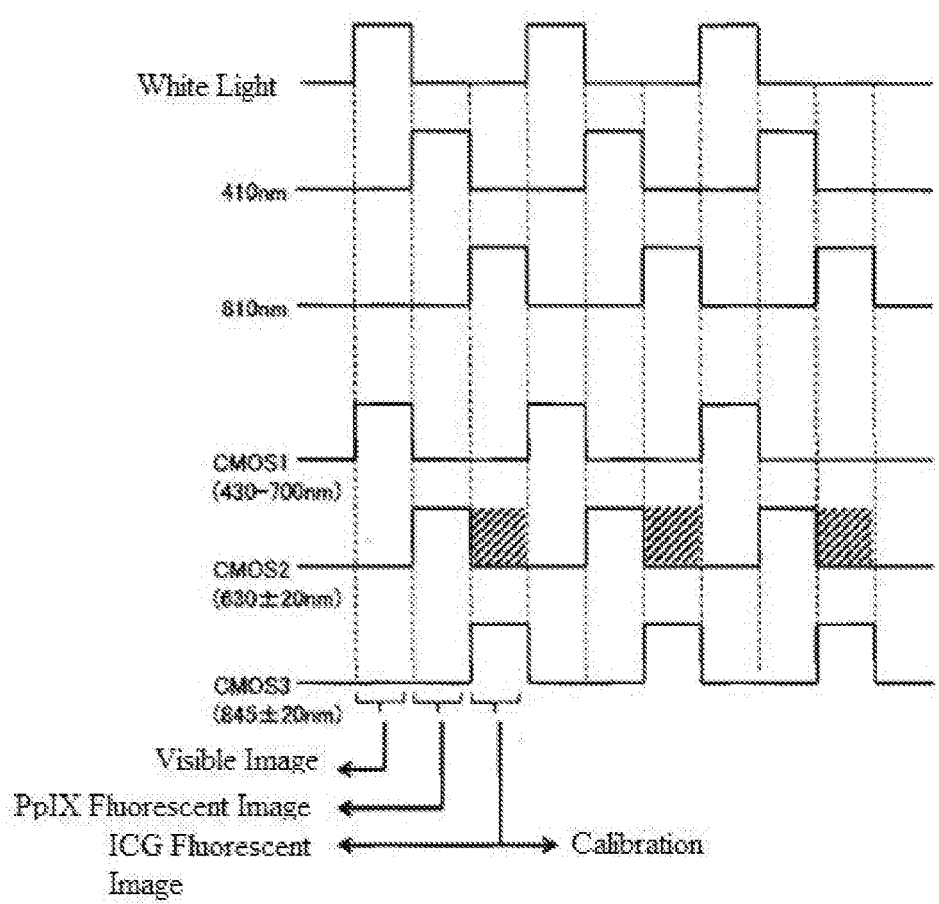

FIG. 5 is a timing chart illustrating the control operations of the first, second, and third light sources 21, 22, and 23, and the first, second, and third imaging elements 31, 32, and 33 when performing imaging using the imaging portion 20 according to the first embodiment according to the present invention.

Figure 6:
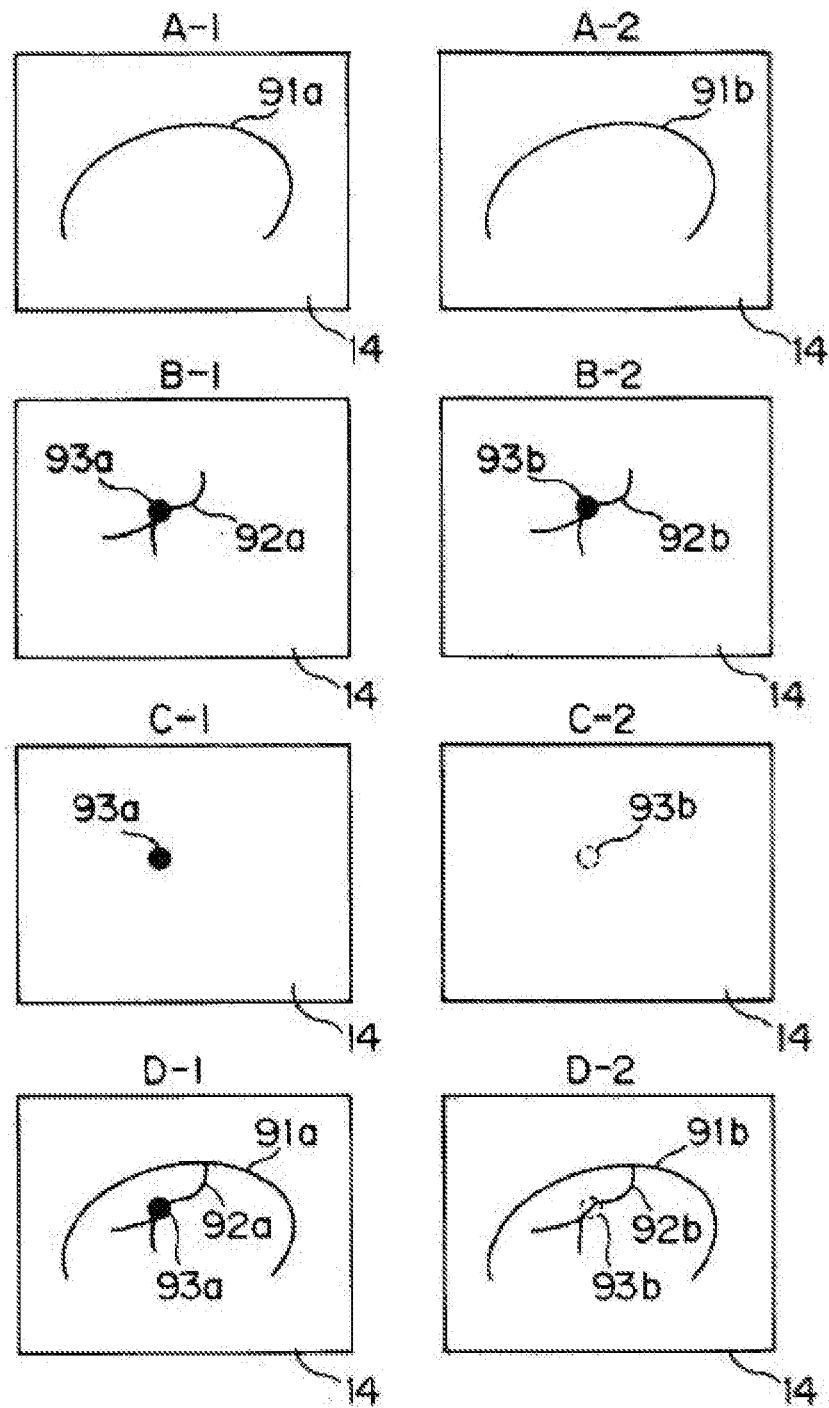

FIG. 6 is a schematic diagram illustrating an image displayed on a displaying portion 14.

Figure 7:
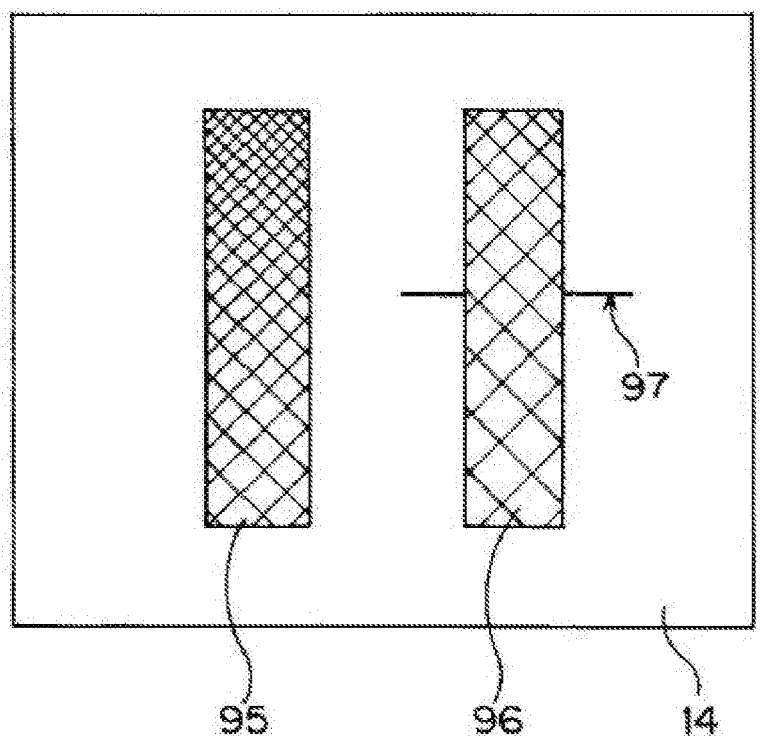

FIG. 7 is a schematic diagram illustrating an evaluation display for evaluating whether or not cancer has spread, based on a red image from PpIX.

Figure 8A:
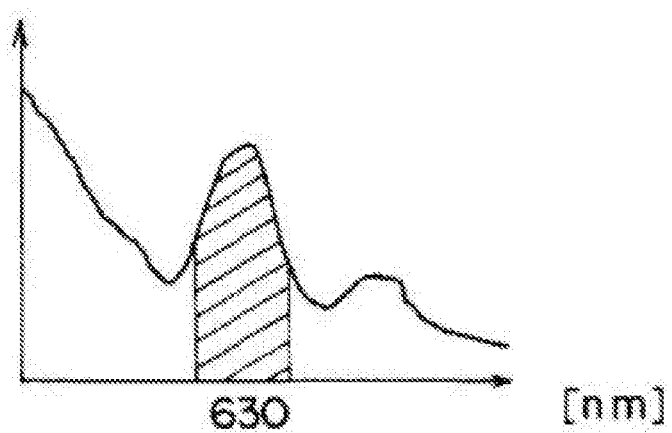
Figure 8B:
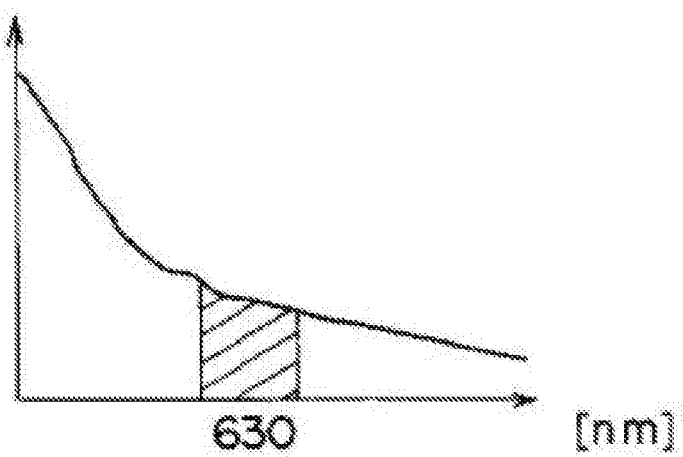
Figure 8C:
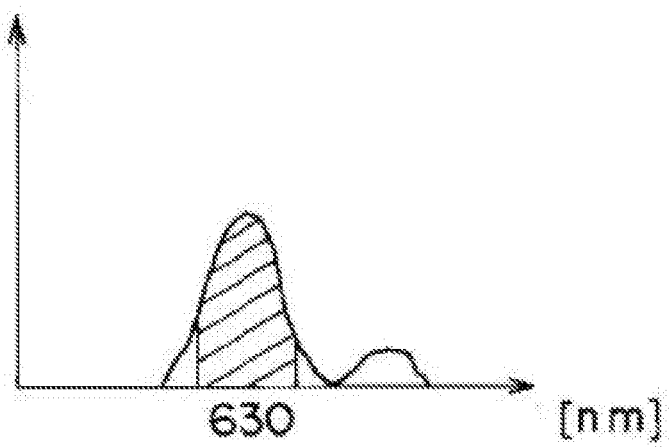

FIGS. 8A to 8C are graphs illustrating the differences between the red light captured by the second imaging element 32 when the second light source 22 is ON and the red light captured by the second imaging element 32 when the second light source 22 is OFF.

Figure 9A:
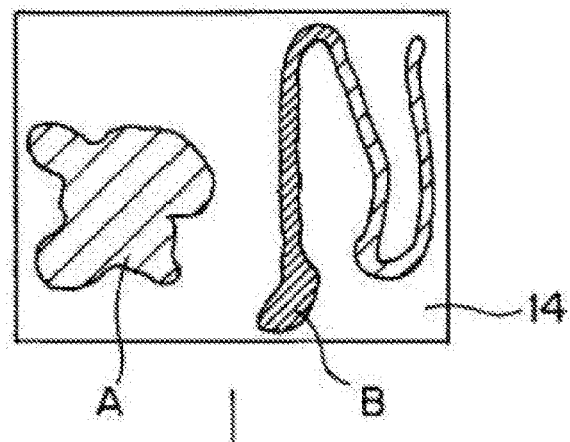
Figure 9B:
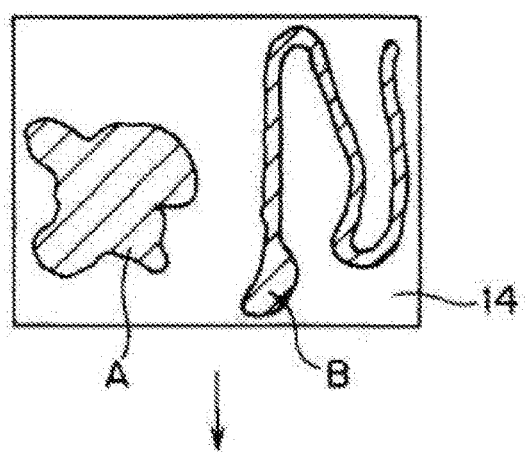
Figure 9C:
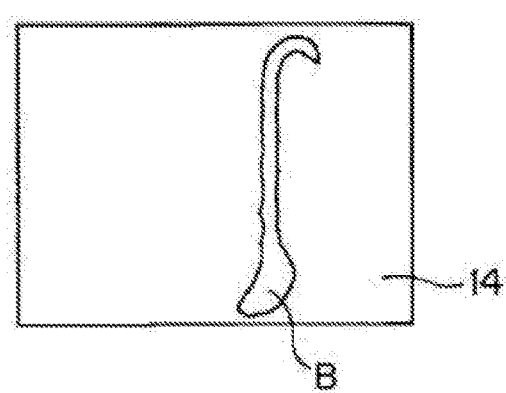

FIGS. 9A to 9C are schematic diagrams of a red image that is displayed on the displaying portion 14 when taking the difference between the red light captured by the second imaging element 32 when the second light source 22 is ON and the red light captured by the second imaging element 32 when the second light source 22 is OFF.

Figure 10:
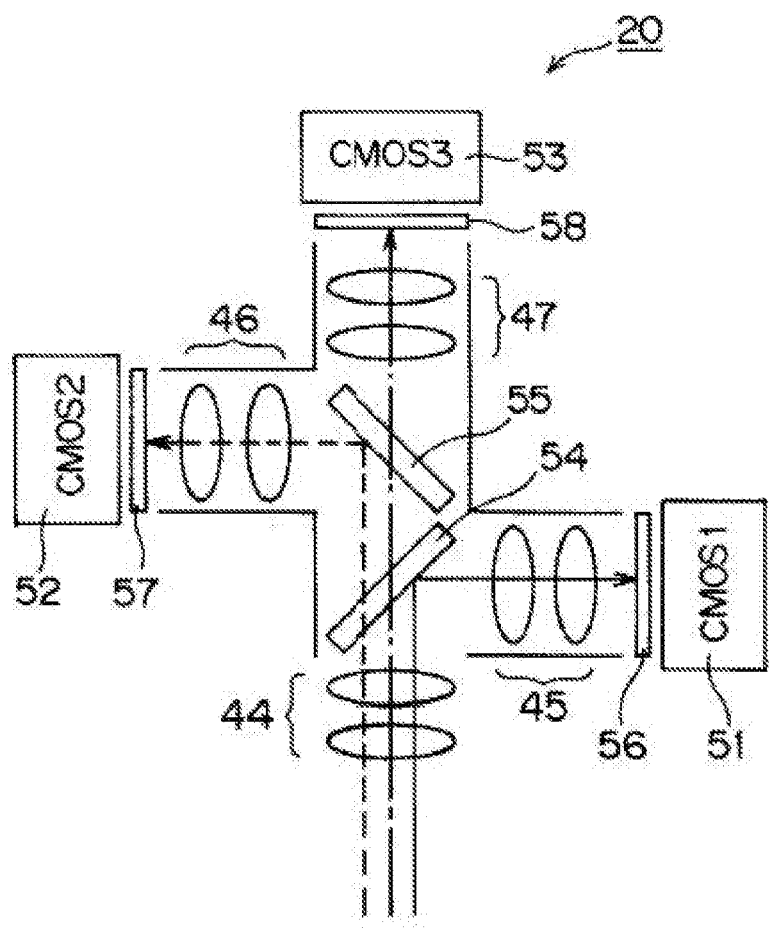

FIG. 10 is a schematic diagram of an imaging portion 20 according to a second embodiment according to the present invention.

Figure 11:
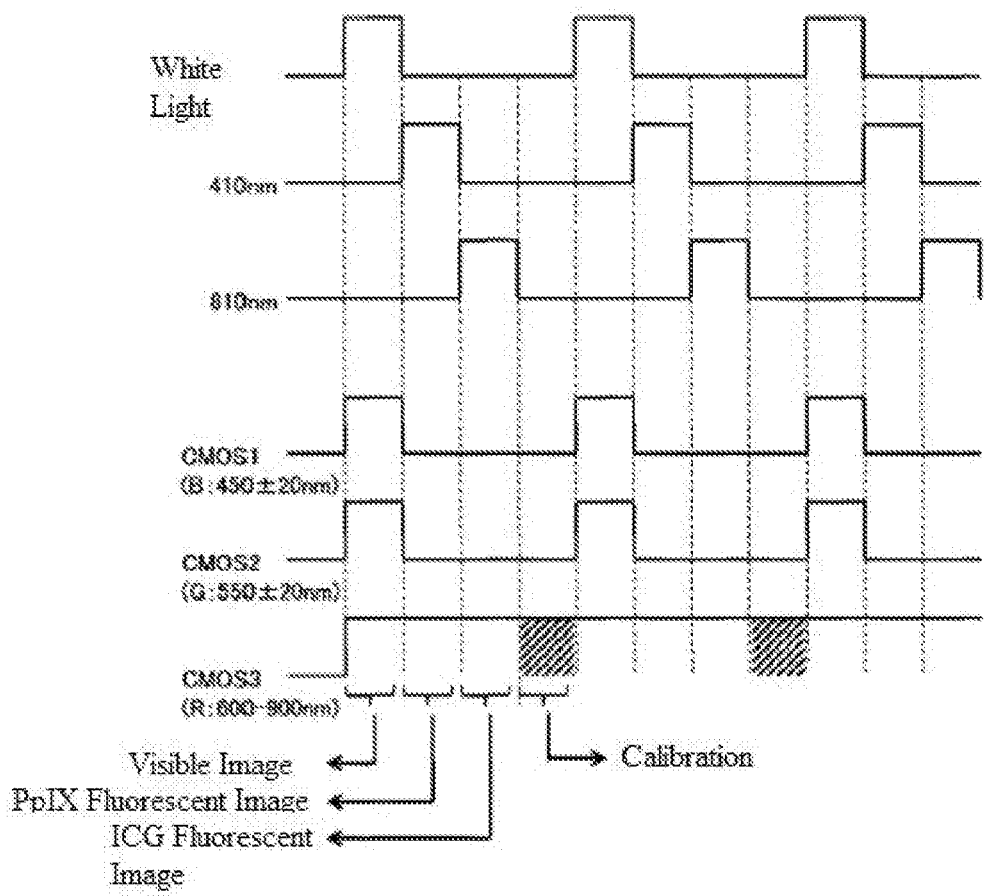

FIG. 11 is a timing chart illustrating the control operations of first, second, and third light sources 21, 22, and 23 and first, second, and third imaging elements 51, 52, and 53 when performing imaging using the imaging portion 20 according to the second embodiment according to the present invention.

Figure 12:
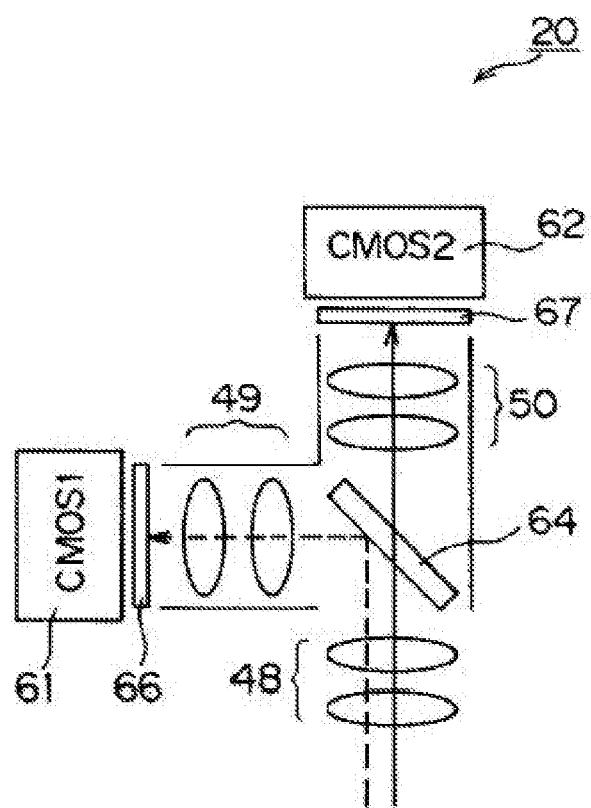

FIG. 12 is a schematic diagram of an imaging portion 20 according to a third embodiment according to the present invention.

Figure 13:
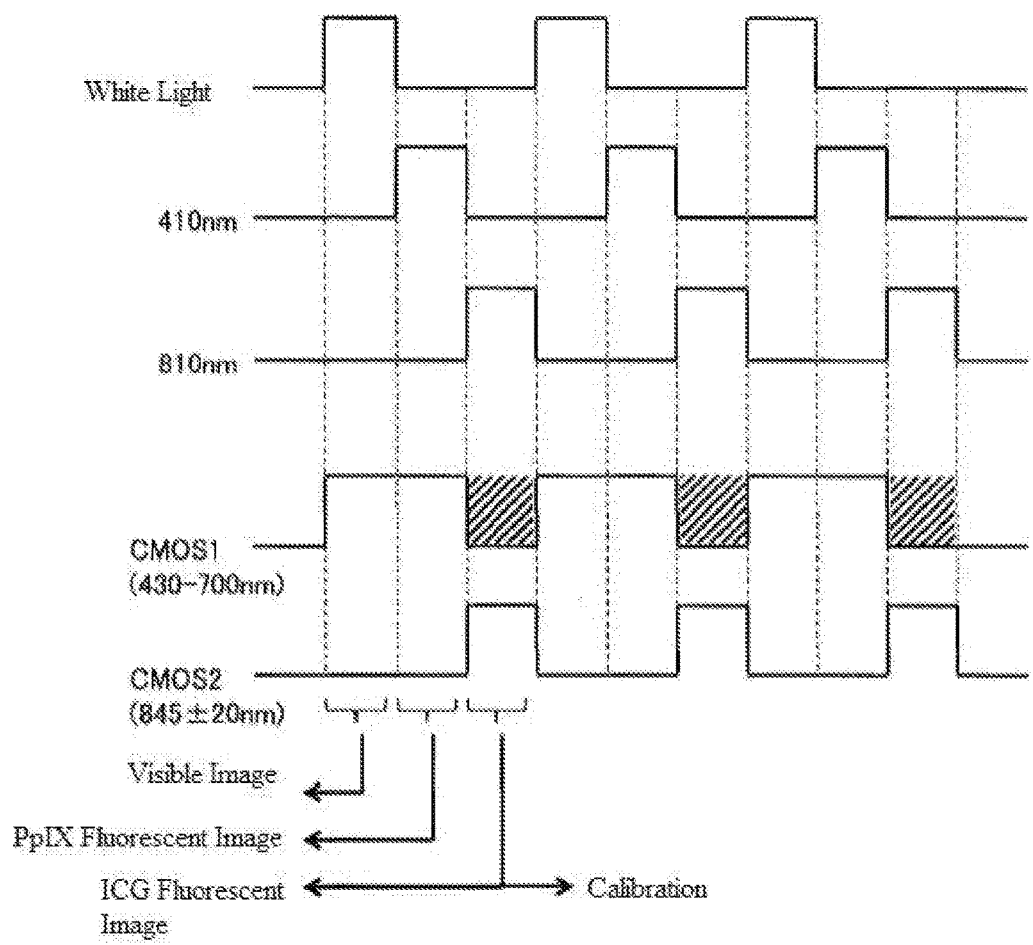

FIG. 13 is a timing chart illustrating the control operations of first, second, and third light sources 21, 22, and 23, and first and second imaging element 61 and 62 when performing imaging using the imaging portion 20 according to the third embodiment according to the present invention.

FORMS FOR CARRYING OUT THE PRESENT INVENTION

Figure 1:
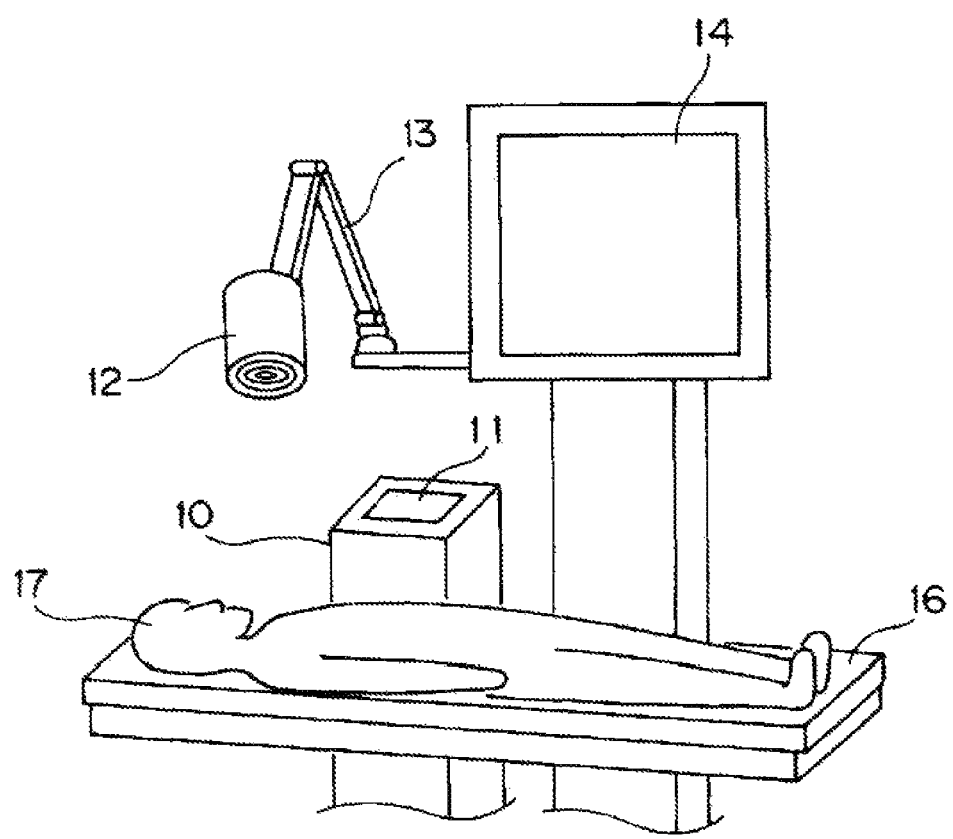
FIG. 1 is a schematic diagram of an imaging device according to the present invention.

Embodiments of the present invention will be explained below based on the figures. FIG. 1 is a schematic diagram of an imaging device according to the present invention.

This imaging device comprises: a main unit 10, which is provided with an inputting device 11 such as a touch panel, and has an image processing portion 100, and the like, included therein; an illuminating/image-capturing portion 12 that is supported movably on an arm 13; a displaying portion 14 that is structured from a liquid crystal display panel, or the like; and a treatment gurney 16 on which a patient 17 is placed. Note that the illuminating/image-capturing portion 12 is not limited to something that is supported on the arm 13, but may instead be carried in the hand of a technician.

Figure 2:
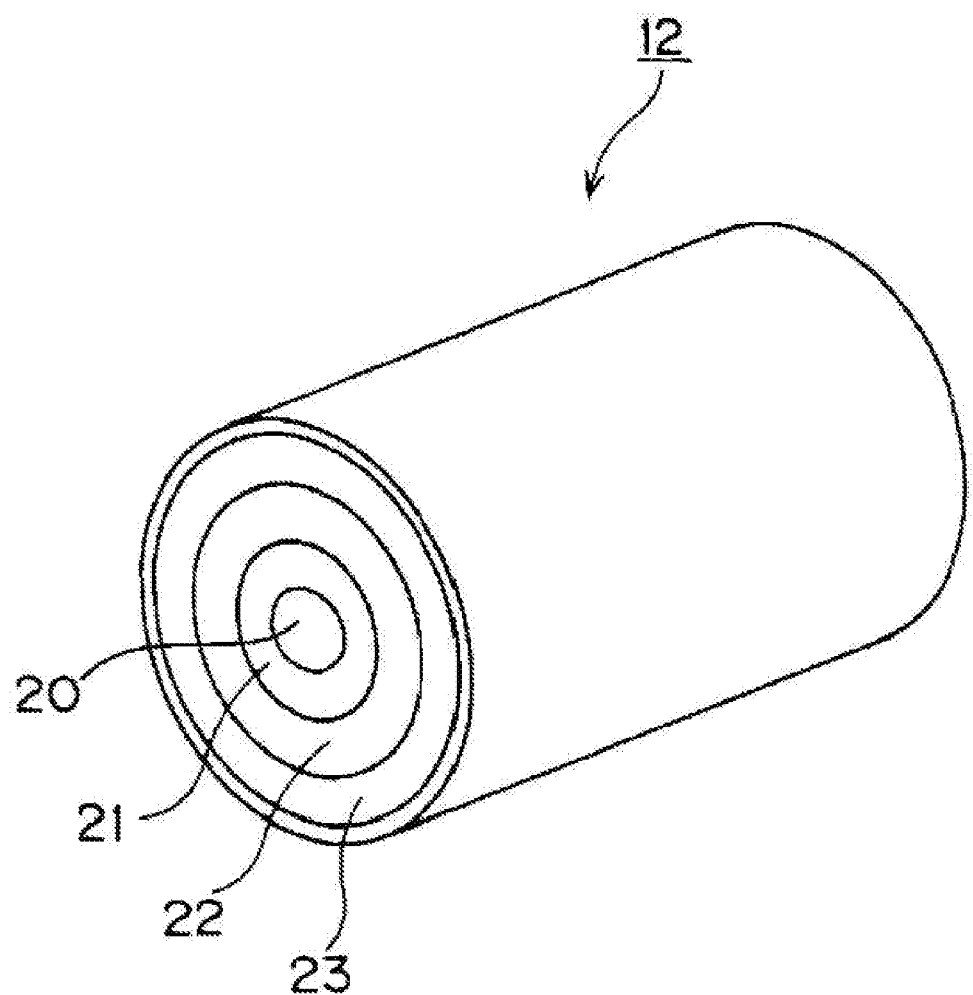
FIG. 2 is a perspective diagram of an illuminating/image-capturing portion 12.

FIG. 2 is a perspective diagram of the illuminating/image-capturing portion 12 described above.

This illuminating/image-capturing portion 12 comprises: an imaging portion 20 comprising a plurality of imaging elements, described below; a first light source 21 that is disposed on an outer peripheral portion of the imaging portion 20; a second light source 22 that is disposed on the outer peripheral portion of the first light source 21; and a third light source 23 that is disposed on the outer peripheral portion of the second light source 22. The first light source 21 emits near-infrared radiation of a wavelength of 810 nm, which is excitation radiation for stimulating indocyanine green as a first fluorescent dye according to the present invention. Near-infrared radiation is emitted, as a first fluorescent light, with a peek at about 845 nm, by the indocyanine green that is illuminated by 810 nm near-infrared radiation. Moreover, the second light source 22 emits a violet light with a wavelength of 410 nm, which is excitation radiation for stimulating PpIX, which is a metabolite of 5-ALA, as a second fluorescent dye according to the present invention. Red light is emitted, as a second fluorescent light, with a peak of about 630 nm, from the PpIX that is illuminated with the 410 nm violet light. Moreover, the third light source 23 emits white light (visible light).

Figure 3:
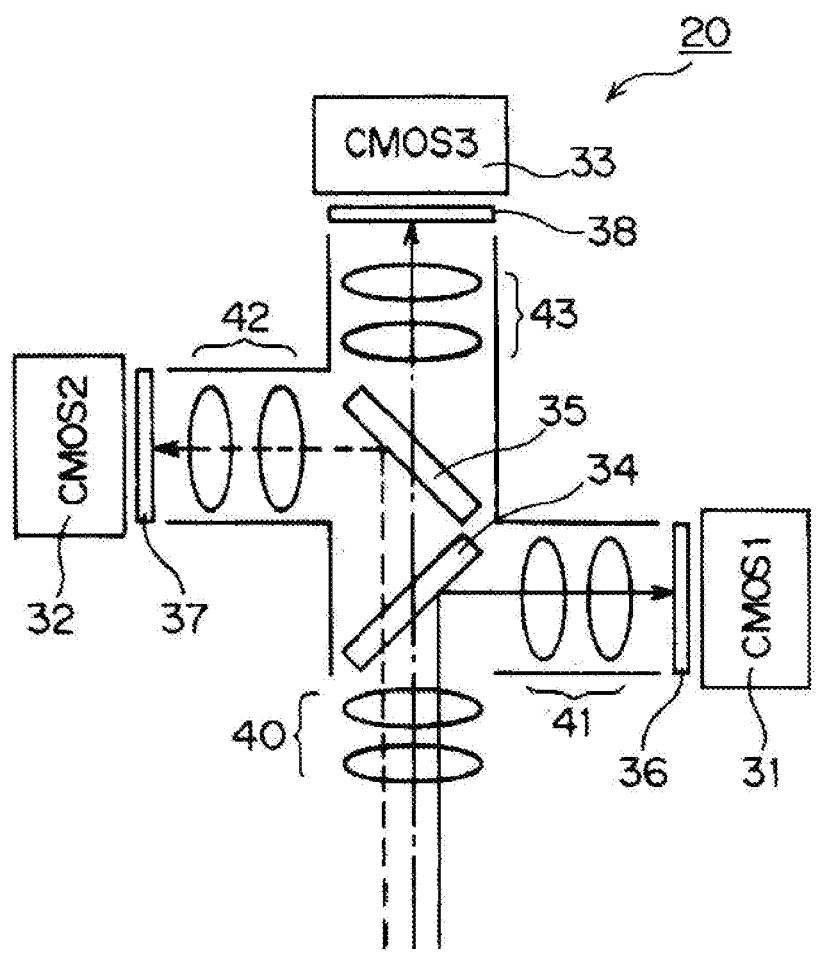
FIG. 3 is a schematic diagram of an imaging portion 20 according to a first embodiment according to the present invention.

FIG. 3 is a schematic diagram of the imaging portion 20 according to the first embodiment according to the present invention.

This imaging portion 20 comprises: a first imaging element 31 that is able to capture visible light; a second imaging element 32 that is able to capture the red light emitted by the PpIX; and a third imaging element 33 that is able to capture near-infrared radiation emitted by the indocyanine green. The first imaging element 31 is able to detect the light of wavelengths between 430 nm and 700 nm of the visible region. Moreover, the second imaging element 32 is able to detect red light, of wavelengths of about ±20 nm centered on 630 nm, which is the wavelength of the red light emitted by the PpIX. Additionally, the third imaging element 33 is able to detect near-infrared radiation of wavelengths of about ±20 nm centered on 845 nm, which is the wavelength of the near-infrared radiation that is emitted by the indocyanine green. These first, second, and third imaging elements 31, 32, and 33 are structured from CMOS image sensors (Complementary Metal Oxide Semiconductor image sensors). Note that Charge Coupled Devices (CCDs) or other imaging elements may be used instead as these first, second, and third imaging elements 31, 32, and 33.

Moreover, the imaging portion 20 comprises a half-mirror 34 that reflects a portion of the visible light that is reflected from the surface of the body of the patient 17 and causes it to be incident into the first imaging element 31, and a dichroic mirror 35 for passing the near-infrared radiation that is emitted by the indocyanine green and that has passed through the half-mirror 34, to cause it to be incident into the third imaging element 33, and also reflects the red light from the PpIX that passes through the half-mirror 34, to cause it to be incident into the second imaging element 32. For the half-mirror 34, one wherein the transmissivity is, for example, about 90% is used. Moreover, as the dichroic mirror 35, one that passes the light of wavelengths longer than 700 nm and that reflects light of wavelengths shorter than 700 nm is used.

Moreover, the imaging portion 20 comprises: a long-pass filter 36 that passes light with wavelengths of 430 nm or more (that is, that blocks the 410 nm violet light that is the excitation radiation for the PpIX), disposed on the front face of the first imaging element 31; a band-pass filter 37 that passes only light of wavelengths near 630 nm, disposed on the front face of the second imaging element 32; and a band-pass filter 38 that passes only light of wavelengths near 810 nm, disposed on the front face of the third imaging element 33. The half-mirror 34 and dichroic mirror 35, the low-pass filter 36, the band-pass filter 37, and the band-pass filter 38 function as the filters according to the present invention.

Moreover, the imaging portion 20 comprises: a lens system 40 that is disposed on the patient 17 side of the half-mirror 34; a lens system 41 that is disposed between the half-mirror 34 and the long-pass filter 36; a lens system 42 that is disposed between the dichroic mirror 35 and the band-pass filter 37; and a lens system 43 that is disposed between the dichroic mirror 35 and the band-pass filter 38.

Figure 4:
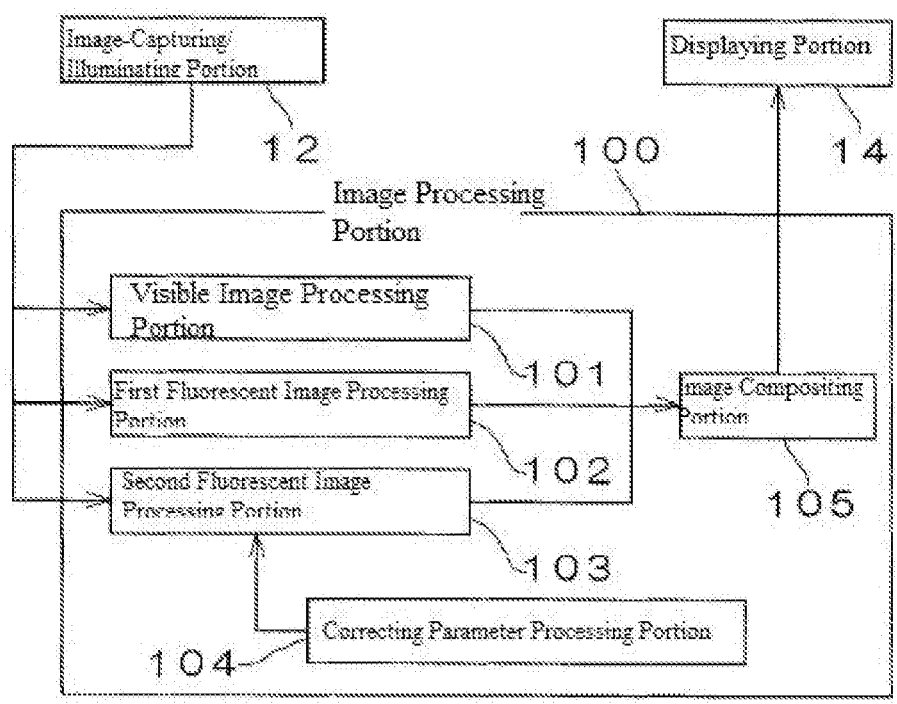
FIG. 4 is a block diagram illustrating the primary controlling system of the imaging device according to the present invention.

FIG. 4 is a block diagram illustrating the primary control system for the imaging device according to the present invention.

The imaging device comprises an image processing portion 100 for displaying, on a displaying portion 14, an image captured by the imaging portion 20 in the illuminating/image-capturing portion 12. The image processing portion 100 is connected to the first, second, and third light sources 21, 22, and 23, and the first, second, and third imaging elements 31, 32, and 33, in the illuminating/image-capturing portion 12. The image processing portion 100 comprises: a visible image processing portion 101 for processing a visible image to be displayed on the displaying portion 14 based on the image captured by the first, second, and third imaging elements 31, 32, and 33; a first fluorescent image processing portion 102 for processing a near-infrared image to be displayed on the displaying portion 14; a second fluorescent image processing portion 103 for processing a red image to be displayed on the displaying portion 14; and an image compositing portion 105 for compositing the visible image, the near-infrared image, and the red image, and displaying the result on the displaying portion 14. Moreover, the image processing portion 100 is provided with a correcting parameter processing portion 104 for correcting the image, using a correcting parameter, when the red image is subjected to image processing in the second fluorescent image processing portion 103.

The imaging operation in the imaging device having the structure described above will be explained next. FIG. 5 is a timing chart illustrating the control operations for the first, second, and third light sources 21, 22, and 23, and the first, second, and third imaging elements 31, 32, and 33 when carrying out imaging using the imaging portion 20 of the first embodiment according to the present invention.

As illustrated in the figure, a series of operations wherein white light is emitted by the third light source 23, after which violet light with a wavelength of 410 nm is emitted by the second light source 22, after which near-infrared radiation with a wavelength of 810 nm is emitted by the first light source 21, is executed at a frame rate of, for example, about 15 fps (frames per second). Given this, timing of imaging by the first, second, and third imaging elements 31, 32, and 33 is controlled using the rising edge signals and falling edge signals of the first, second, and third light sources 21, 22, and 23 as trigger signals.

That is, when the third light source 23 is ON, the visible light that is reflected on the surface of the body of the patient 17 is captured by the first imaging element 31. This visible image is subjected to image processing by the visible image processing portion 101 illustrated in FIG. 4. Moreover, when the second light source 22 is ON, the red light that is emitted by the PpIX is captured by the second imaging element 32. This red image is subjected to image processing by the second fluorescent image processing portion 103 illustrated in FIG. 4. Moreover, when the first light source 21 is ON, the near-infrared light that is emitted by the indocyanine green is captured by the third imaging element 33. This near-infrared image is subjected to image processing by the first fluorescent image processing portion 102.

At this time, through the effect of the long-pass filter 36 that is disposed on the front face of the first imaging element 31, only light with wavelengths of 430 nm or more will arrive at the first imaging element 31 and the 410 nm violet light that is the excitation radiation for the PpIX is blocked, and thus a high-quality visible image of the patient 17 is captured by the first imaging element 31. Moreover, through the effect of the band-pass filter 37 that is disposed on the front face of the second imaging element 32, only light with wavelengths near 630 nm, which is the light from the PpIX, will arrive at the second imaging element 32, and thus a high-quality red image from the PpIX is captured by the second imaging element 32. Similarly, through the effect of the band-pass filter 38 that is disposed on the front face of the third imaging element 33, only light of wavelengths near 810 nm, which is fluorescent light from the indocyanine green, will arrive at the third imaging element 33, and thus a high-quality near-infrared image from the indocyanine green will be captured by the third imaging element 33.

Image processing, such as gamma correction, edge enhancement processing, color correction, and the like are performed in the visible image processing portion 101, the second fluorescent image processing portion 103, and the first fluorescent image processing portion 102. At this time, the edge enhancement processing is performed primarily on the red image from the PpIX and the near-infrared image from the indocyanine green. Moreover, the color adjusting processing performs a colorizing process to turn the visible image, the red image, and the near-infrared image into monochromatic images of different colors. These images are composited by the image compositing portion 105, to produce a composite image.

FIG. 6 is a schematic diagram illustrating an image that is displayed at this time on the displaying portion 14.

In this diagram, A-1 and A-2 show schematically the visible image of the surface of the body of the patient 17, B-1 and B-2 show schematically the near-infrared image from the indocyanine green, C-1 and C-2 show schematically the red image from the PpIX, and D-1 and D-2 show schematically the composite (fusion) image thereof. Moreover, in this figure, 91a and 91b show the patient 17 schematically, 92a and 92b show lymph ducts schematically, and 93a and 93b show lymph nodes schematically. Given this, A-1, B-1, C-1, and D-1 show a case wherein the cancer has spread to the lymph nodes 93a, and A-2, B-2, C-2, and D-2 show a case wherein the cancer has not spread to the lymph nodes 93b.

As illustrated in this diagram, the positions of the lymph ducts can be seen in the near-infrared image from the indocyanine green, and whether or not a tumor (a cancer) exists can be seen in the red image from the PpIX. Moreover, the overall positional relationships can be seen in the composite image thereof. At this time, if the cancer has spread to the lymph node 93a, the lymph node 93a will be displayed more intensely, as illustrated in C-1 and D-1, due to the accumulation of PpIX at that location, and if the cancer has not spread to the lymph node 93b, the lymph node 93b will be displayed faintly, as illustrated in C-2 and D-2, because of the lack of accumulation of PpIX.

Moreover, at this time the positions of the red image from the PpIX and the near-infrared image from the indocyanine green are compared to evaluate whether or not the two are overlapping. That is, even if an accumulation of PpIX can be seen in the red image, if no accumulation of indocyanine green can be seen in the near-infrared image, this suggests the possibility that the cancer has not spread, but that there is a false positive due to inflammation, or the like. On the other hand, if there are accumulations of PpIX and indocyanine green at the same location, it can then be concluded that there is a high probability that the cancer has spread.

FIG. 7 is a schematic diagram illustrating an evaluation display for evaluating whether or not cancer has spread, based on the red image from the PpIX.

In this evaluation display, the various images shown in FIG. 6 are displayed selectively on the displaying portion 14. Note that the evaluation display may display the various images shown in FIG. 6, superimposed on each other. In this evaluation display, reference code 95 indicates the intensity of the red image, from the PpIX, in the regions of the lymph nodes 93a and 93b, and reference code 96 indicates a high probability that there is cancer in that region. The probability of whether or not there is cancer is evaluated based on parameters such as the intensity of the red image from the PpIX, and the locations of concentration of the PpIX and of the indocyanine green. Given this, reference code 97 indicates a threshold value criterion for whether or not there is cancer in that region. Displaying on the displaying portion 14 in this way makes it possible for even an inexperienced operator to understand intuitively whether or not the cancer has spread.

When the intensity of the red image from the PpIX is used to evaluate whether or not there is cancer in a region, the intensity of the red image from the PpIX will vary depending on a variety of parameters. Because of this, in the imaging device according to the present invention the red image from the PpIX is corrected based on correcting parameters that have been set in advance, in a correcting parameter processing portion 104 in the image processing portion 100.

The distance between the imaging portion 20 of the illuminating/image-capturing portion 12 and the patient 17, the per-unit-area and per-unit-time illumination intensity of the excitation radiation on the PpIX by the second light source 22, the properties of the second imaging element 32, information on the density of the red image from the PpIX measured at the time of calibration, described below, the density of the red image by the PpIX in a cancerous region, measured empirically in advance, and the like, may be used as these parameters.

The red image from the PpIX may be affected by the lighting in the operating theater when the imaging device is used in, for example, an open-abdominal operation, where, for example, light of a wavelength of about 630 nm, which is a fluorescent light from the PpIX, is also emitted by the fluorescent lights, white LEDs, and the like, in the operating theater. Because of this, this component of the illumination of the operating theater will also be superimposed on the red image that is captured by the second imaging element 32. While this problem would be solved by having the operating theater be a dark room, performing the operation itself would be impossible. Because of this, in the imaging device according to the present invention, a structure is used wherein the red image from the PpIX is formed from the difference between the red image when the second light source 22 is ON and the red image when the second light source 22 is OFF.

That is, in the timing chart illustrated in FIG. 5, in the imaging device according to the present invention the second imaging element 32 not only perform an imaging operation when the second light source 22 is ON, but also, as illustrated by the hatching in FIG. 5, performs an imaging operation, for calibration, when the first light source 21 and the second light source 22 are OFF. Additionally, the second fluorescent image processing portion 103 in the image processing portion 100 uses a structure wherein the red image is formed from the difference between the red light that is captured by the second imaging element 32 when the second light source 22 is ON and the red light that is captured by the second imaging element 32 when the second light source 22 is OFF.

FIGS. 8A to 8C are graphs illustrating the state when taking the difference between the red light captured by the second imaging element 32 when the second light source 22 is ON and the red light captured by the second imaging element 32 when the second light source 22 is OFF, and FIGS. 9A to 9C are schematic diagrams of the red image that is displayed on the imaging portion 14 at this time. Note that, in FIGS. 8A to 8C, the horizontal axis indicates the wavelength of light, and the vertical axis indicates the intensity of the fluorescent light (arbitrary units).

When a red image from the PpIX is captured by the second imaging element 32 in a state wherein the second light source 22 is ON, red light wherein the wavelengths peak at 630 nm, which is fluorescent light from the PpIX, and the illumination light that includes the wavelength of 630 nm, emitted by the fluorescent lights or white LEDs in the operating theater, are superimposed and captured by the second imaging element 32, as illustrated in FIG. 8A and FIG. 9A. In this state, image A and image B are displayed on the displaying portion 14.

Following this, in order to perform calibration, a red image is captured by the second imaging element 32 in a state wherein the second light source 22 is OFF, as illustrated by the hatching in FIG. 5. At this time, as illustrated in FIG. 8B and FIG. 9B, only the illumination light that includes the wavelength of 630 nm, emitted by the fluorescent lights or white LEDs in the operating theater, is captured. In this state as well, the image A and image B are displayed on the displaying portion 14. Note that while, at this time, the first light source 21 is ON, as illustrated in FIG. 5, the near-infrared radiation with a wavelength of 810 nm, from the first light source 21, does not arrive at the second imaging element 32 due to the effects of the dichroic mirror 35 and the band-pass filter 37.

Additionally, true red images from the fluorescence from the PpIX can be obtained, as illustrated in FIG. 8C and FIG. 9C, through subtracting the red images in FIG. 8B and FIG. 9B from the red images in FIG. 8A and FIG. 9A. In this state, the image A is eliminated through this subtraction, so that only the image B will be displayed on the displaying portion 14.

In this way, the red image from the PpIX can be produced more faithfully through the difference between the red image when the second light source 22 is ON and the red image when the second light source 22 is OFF.

Another embodiment according to the present invention will be explained next. FIG. 10 is a schematic diagram of an imaging portion 20 according to a second embodiment according to the present invention. Note that the structures aside from that of the imaging element 20 are identical to those in the first embodiment, described above.

The imaging portion 20 according to the second embodiment comprises: a first imaging element 51 that is able to capture blue (B) light with wavelengths of about ±20 nm centered on 450 nm; a second imaging element 52 that is able to capture green (G) light with wavelengths of about 550 nm±20 nm; and a third imaging element 53 that is able to capture near-infrared radiation, from the red (R) light, with wavelengths between about 600 nm and 900 nm.

Moreover, the imaging element 20 comprises: a dichroic mirror 54 that passes that portion of the light with which the patient 17 is illuminated that has wavelengths longer than 480 nm, and that reflects light of wavelengths less than 480 nm to cause it to be incident into the first imaging element 51; and a dichroic mirror 55 that passes light with wavelengths longer than 580 nm that has passed through the dichroic mirror 54 to cause it to be incident into the third imaging element 53, and reflects light with wavelengths of less than 580 nm to cause it to be incident into the second imaging element 52.

Moreover, the imaging portion 20 comprises: a band-pass filter 56 that passes only light with wavelengths near 450 nm, disposed on the front face of the first imaging element 51; a band-pass filter 57 that passes only light with wavelengths near 550 nm, disposed on the front face of the second imaging element 52; and a long-pass filter 58 that passes only light with wavelengths of above 600 nm, disposed on the front face of the third imaging element 53. The dichroic mirror 54 and dichroic mirror 55, the band-pass filter 56, the band-pass filter 57, and the long-pass filter 58 function as the filters according to the present invention.

Furthermore, the imaging portion 20 comprises: a lens system 44 that is disposed on the patient 17 side of the dichroic mirror 54; a lens system 45 that is disposed between the dichroic mirror 54 and the band-pass filter 56; a lens system 46 that is disposed between the dichroic mirror 55 and the band-pass filter 57; and a lens system 47 that is disposed between the dichroic mirror 55 and the long-pass filter 58.

FIG. 11 is a timing chart illustrating the control operations of the first, second, and third light sources 21, 22, and 23, and of the first, second, and third imaging element 51, 52, and 53 when carrying out imaging using the imaging portion 20 according to the second embodiment according to the present invention, illustrated in FIG. 10.

As illustrated in the figure, a series of operations wherein white light is emitted by the third light source 23, after which violet light with a wavelength of 410 nm is emitted by the second light source 22, after which near-infrared radiation with a wavelength of 810 nm is emitted by the first light source 21, is executed at a frame rate of, for example, about 15 fps (frames per second). Given this, timing of imaging by the first, second, and third imaging elements 51, 52, and 53 is controlled using the rising edge signals and falling edge signals of the first, second, and third light sources 21, 22, and 23 as trigger signals. However, in the second embodiment, a lag time, for calibration, is provided between turning OFF the first light source 21 and turning it ON the third light source 23.

In the imaging portion 20 according to the second embodiment, when the third light source 23 is ON, the blue (B) component of the visible light that is reflected from the surface of the body of the patient 17 is captured by the first imaging element 51, the green (G) component of the visible light that is reflected from the surface of the body of the patient 17 is captured by the second imaging element 52, and the red (R) component of the visible light that is reflected from the surface of the body of the patient 17 is captured by the third imaging element 53. These measured values for the visible image are subjected to image processing by the visible image processing portion 101 illustrated in FIG. 4.

Moreover, when the second light source 22 is ON, the red light that is emitted by the PpIX is captured by the third imaging element 53. This red image is subjected to image processing by the second fluorescent image processing portion 103 illustrated in FIG. 4. Moreover, when the first light source 21 is ON, the near-infrared radiation that is emitted by the indocyanine green is captured by the third imaging element 53. This near-infrared image is subjected to image processing by the first fluorescent image processing portion 102.

At this time, only light with wavelengths near 450 nm will arrive at the first imaging element 51 because of the effect of the band-pass filter 56 that is disposed on the front face of the first imaging element 51, only light with wavelengths near 550 nm will arrive at the second imaging element 52 because of the effect of the band-pass filter 57 that is disposed on the front face of the second imaging element 52, and only light with wavelengths above 600 nm will arrive at the third imaging element 53 because of the effect of the long-pass filter 58 that is disposed on the front face of the third imaging element 53, so that a visible image, a red image from the PpIX, and a near-infrared image from the indocyanine green will be captured.

Moreover, in this second embodiment, in a state wherein the first, second, and third light sources 21, 22, and 23 are OFF, the red image is captured by the second imaging element 32, in order to perform calibration, as indicated by the hatching in FIG. 11. Moreover, in the same manner as in the first embodiment, described above, a structure is used wherein the red image from the PpIX is formed by taking the difference between the red image when the second light source 22 is ON and the red image when the first, second, and third light sources 21, 22, and 23 are OFF. This enables the red image from the PpIX to be produced more faithfully, in the same way as in the first embodiment.

Yet another embodiment according to the present invention will be explained next. FIG. 12 is a schematic diagram of an imaging portion 20 according to a third embodiment according to the present invention. Note that the structures aside from that for the imaging portion 20 are identical to those in the first and second embodiments.

The imaging portion 20 according to the third embodiment comprises: a first imaging element 61 that is able to capture light of wavelengths between 430 nm and 700 nm; and a second imaging element 62 that is able to detect light of wavelengths of about ±20 nm, centered on 845 nm, of the near-infrared radiation emitted by the indocyanine green.

Moreover, this imaging portion 20 is provided with a dichroic mirror 64 for passing that portion of the light emitted by the patient 17 that has wavelengths longer than 700 nm, to be incident into the second imaging element 62, and to reflect that light that has wavelengths shorter than the 700 nm, to be incident into the first imaging element 61.

Moreover, the imaging portion 20: comprises a long-pass filter 66 that passes only light of wavelengths above 430 nm, disposed on the front face of the first imaging element 61; and a band-pass filter 67 that passes only light with wavelengths near 845 nm, disposed on the front face of the second imaging element 62. The dichroic mirror 64, and the long-pass filter 66 and band-pass filter 67, function as the filters according to the present invention.

Moreover, the imaging portion 20: comprises a lens system 48 that is disposed on the patient 17 side of the dichroic mirror 64; a lens system 49 that is disposed between the dichroic mirrors 64 and the long-pass filter 66; and a lens system 50 that is disposed between the dichroic mirror 64 and the band-pass filter 67.

FIG. 13 is a timing chart illustrating the control operations of first, second, and third light sources 21, 22, and 23, and first and second imaging element 61 and 62 when performing imaging using the imaging portion 20 according to the third embodiment according to the present invention, illustrated in FIG. 12.

As illustrated in the figure, a series of operations wherein white light is emitted by the third light source 23, after which violet light with a wavelength of 410 nm is emitted by the second light source 22, after which near-infrared radiation with a wavelength of 810 nm is emitted by the first light source 21, is executed at a frame rate of, for example, about 15 fps (frames per second). Given this, timing of imaging by the first and second imaging elements 61 and 62 is controlled using the rising edge signals and falling edge signals of the first, second, and third light sources 21, 22, and 23 as trigger signals.

In the image processing portion 20 according to the third embodiment, when the third light source 23 is ON, the visible light that is reflected from the surface of the body of the patient 17 is captured by the first imaging element 61. The measured values for the visible image are subjected to image processing by the visible image processing portion 101 illustrated in FIG. 4. Moreover, when the second light source 22 is ON, red light, emitted by the PpIX, is captured from the R component of the first imaging element 61. This red image is subjected to image processing by the second fluorescent image processing portion 103 illustrated in FIG. 4. Moreover, when the first light source 21 is ON, the near-infrared radiation that is emitted by the indocyanine green is captured by the second imaging element 62. This near-infrared image is subjected to image processing by the first fluorescent image processing portion 102.

At this time, because of the effect of the long-pass filter 66 that is disposed on the front face of the first imaging element 61, only light with wavelengths greater than 430 nm will arrive at the first imaging element 61, and the 410 nm violet light that is the excitation radiation for the PpIX is blocked. Moreover, because of the effect of the band-pass filter 67 that is disposed on the front face of the second imaging element 62, only light with wavelengths near 845 nm will arrive at the second imaging element 62. Because of this, the visible image, the red image from the PpIX, and the near-infrared image from the indocyanine green will be captured with high quality.

Moreover, in the third embodiment, calibration is performed in a state wherein the second and third light sources 22 and 23 are OFF, as indicated by the hatching in FIG. 13, the red image is captured using only the R component of the first imaging element 61. Moreover, in the same manner as with the first and second embodiments, described above, a structure is used wherein the red image from the PpIX is produced through the difference between the red image when the second light source 22 is ON and the red image when the second and third light sources 22 and 23 are OFF. This enables the red image from the PpIX to be produced more faithfully, in the same manner as in the first and second embodiments.

EXPLANATIONS OF REFERENCE CODES

12: Illuminating/Image-Capturing Portion
14: Displaying Portion
17: Patient
20: Imaging Portion
21: First Light Source
22: Second Light Source
23: Third Light Source
31: First Imaging Element
32: Second Imaging Element
33: Third Imaging Element
34: Half-Mirror
35: Dichroic Mirror
36: Long-Pass Filter
37: Band-Pass Filter
38: Band-Pass Filter
51: First Imaging Element
52: Second Imaging Element
53: Third Imaging Element
54: Dichroic Mirror
55: Dichroic Mirror
56: Band-Pass Filter
57: Band-Pass Filter
58: Long-Pass Filter
61: First Imaging Element
62: Second Imaging Element
64: Dichroic Mirror
66: Long-Pass Filter
67: Band-Pass Filter
100: Image Processing Portion
101: Visible Image Processing Portion
102: First Fluorescent Image Processing Portion
103: Second Fluorescent Image Processing Portion
104: Correcting Parameter Processing Portion
105: Image Compositing Portion

What is claimed:

1. An imaging device wherein a first fluorescent dye that emits light through being illuminated with excitation radiation, and a second fluorescent dye that emits light through being illuminated with excitation radiation, and that has the nature of a metabolite thereof accumulating in a tumor, are adapted to be placed in the body of a patient, and fluorescent light from the first fluorescent dye and fluorescent light from the second fluorescent dye are imaged, comprising:
- a first light source configured to emit, toward the patient, light of a first wavelength for stimulating the first fluorescent dye;
- a second light source configured to emit, toward the patient, light of a second wavelength, different from the first wavelength, for stimulating the second fluorescent dye;
- a third light source configured to emit, toward the patient, a white light;
- a plurality of imaging elements;
- a filter configured to selectively cause first fluorescent light that is emitted by the first fluorescent dye, second fluorescent light that is emitted by the second fluorescent dye, and visible light that is reflected by the patient, to be incident into the plurality of imaging elements; and
- an image processing portion configured to display a first fluorescent image, a second fluorescent image, and a visible image on a displaying portion based on the first fluorescent light, the second fluorescent light, and the visible light captured by the plurality of imaging elements through the filter, wherein
the image processing portion generates the second fluorescent image through taking a difference between the light of wavelengths corresponding to the second fluorescent light when the second light source is ON and the light of wavelengths corresponding to the second fluorescent light when the second light source is OFF.

2. An imaging device as set forth in claim 1, wherein:
the image processing portion comprises a correcting parameter processing portion for correcting the second fluorescent image through a correcting parameter that has been set in advance.

3. An imaging device as set forth in claim 1, wherein:
the first fluorescent dye, through being illuminated with the excitation radiation, emits infrared radiation as the fluorescent light, and the second fluorescent dye, through illumination with the excitation radiation, emits visible light as the fluorescent light;
the plurality of imaging elements include a first imaging element able to capture visible light, a second imaging element able to capture the second fluorescent light that is emitted by the second fluorescent dye, and a third imaging element able to capture the first fluorescent light emitted by the first fluorescent dye;
the filter includes a half-mirror configured to reflect a portion of the visible light, reflected by the patient, to cause the visible light to be incident into the first imaging element, and a dichroic mirror configured to pass the first fluorescent light that has passed through the aforementioned half-mirror to cause the first fluorescent light to be incident into the third imaging element, and to reflect the second fluorescent light, which has passed through the aforementioned half-mirror, to cause the second fluorescent light to be incident into the second imaging element;
the image processing portion includes a visible image processing portion configured to perform image processing on the visible light captured by the first imaging element to display the visible light as the visible image on the displaying portion, a second fluorescent image processing portion configured to perform image processing on the second fluorescent light, captured by the second imaging element, to display the second fluorescent light as the second fluorescent image on the displaying portion, and a first fluorescent image processing portion configured to perform image processing on the first fluorescent light, captured by the third imaging element, to display the first fluorescent light as the first fluorescent image on the displaying portion;
the visible image processing portion performs image processing on the visible light reflected from the patient when the third light source is ON to display the visible light as the visible image on the displaying portion;
the second fluorescent image processing portion performs image processing on the second fluorescent light that is emitted by the second fluorescent dye when the second light source is ON, to display the second fluorescent light as the second fluorescent image on the displaying portion; and
the first fluorescent image processing portion performs image processing on the first fluorescent light that is emitted by the first fluorescent dye when the first light source is ON, to display the first fluorescent light as the first fluorescent image on the displaying portion.

4. An imaging device as set forth in claim 1, wherein:
the first fluorescent dye, through being illuminated with the excitation radiation, emits infrared radiation as the fluorescent light, and the second fluorescent dye, through illumination with the excitation radiation, emits visible light as the fluorescent light;
the plurality of imaging elements include a first imaging element able to capture light of blue wavelengths, a second imaging element able to capture light of green wavelengths, and a third imaging element able to capture light of red wavelengths or longer;
the filter includes a first dichroic mirror configured to reflect light of a blue wavelength, to cause the light of the blue wavelength to be incident into the first imaging element, and a second dichroic mirror configured to pass light of a red wavelength or longer, which has passed through the first dichroic mirror, to cause the light of the red wavelength or longer to be incident into the third imaging element, and to reflect light of a green wavelength, which has passed through the first dichroic mirror, to cause the light of the green wavelength to be incident into the second imaging element;
the image processing portion includes a visible image processing portion configured to perform image processing on the light captured by the first, second, and third imaging element to display the light as the visible image on the displaying portion, a second fluorescent image processing portion configured to perform image processing on the second fluorescent light, captured by the third imaging element, to display the second fluorescent light as the second fluorescent image on the displaying portion, and a first fluorescent image processing portion configured to perform image processing on the first fluorescent light, captured by the second imaging element, to display the first fluorescent light as the first fluorescent image on the displaying portion;
the visible image processing portion performs image processing on the visible light reflected from the patient when the third light source is ON to display the visible light as the visible image on the displaying portion;
the second fluorescent image processing portion performs image processing on the second fluorescent light that is emitted by the second fluorescent dye when the second light source is ON, to display the second fluorescent light as the second fluorescent image on the displaying portion; and the first fluorescent image processing portion performs image processing on the first fluorescent light that is emitted by the first fluorescent dye when the first light source is ON, to display the first fluorescent light as the first fluorescent image on the displaying portion.

5. An imaging device as set forth in claim 1, wherein:

the first fluorescent dye, through being illuminated with the excitation radiation, emits infrared radiation as the fluorescent light, and the second fluorescent dye, through illumination with the excitation radiation, emits visible light as the fluorescent light;

the plurality of imaging elements includes a first imaging element that is able to capture visible light and a second imaging element that is able to capture infrared radiation;

the filter includes a dichroic mirror that reflects the visible light, reflected from the patient, and the second fluorescent light that is emitted by the second fluorescent dye, and that passes the first fluorescent light that is emitted by the first fluorescent dye;

the image processing portion includes a visible image processing portion configured to perform image processing on the visible light captured by the first imaging element to display the visible light as the visible image on the displaying portion, a second fluorescent image processing portion configured to perform image processing on the second fluorescent light, captured by the first imaging element, to display the second fluorescent light as the second fluorescent image on the displaying portion, and a first fluorescent image processing portion configured to perform image processing on the first fluorescent light, captured by the second imaging element, to display the first fluorescent image on the displaying portion;

the visible image processing portion performs image processing on the visible light reflected from the patient when the third light source is ON to display the visible light as the visible image on the displaying portion;

the second fluorescent image processing portion performs image processing on the second fluorescent light that is emitted by the second fluorescent dye when the second light source is ON, to display the second fluorescent light as the second fluorescent image on the displaying portion; and the first fluorescent image processing portion performs image processing on the first fluorescent light that is emitted by the first fluorescent dye when the first light source is ON, to display the first fluorescent light as the first fluorescent image on the displaying portion.

6. An imaging device as set forth in claim 1 comprising:

an image compositing portion configured to composite and display on to the displaying portion the first fluorescent image, the second fluorescent image, and the visible image.

7. An imaging device as set forth in claim 1, wherein:

the first fluorescent dye is indocyanine green, or the second fluorescent dye is 5-aminolevulinic acid.

8. An imaging method comprising:

emitting, toward a patient, light of a first wavelength for stimulating a first fluorescent dye that emits light through being illuminated with excitation radiation;

emitting, toward the patient, light of a second wavelength, different from the first wavelength, for stimulating a second fluorescent dye that emits light through being illuminated with excitation radiation, and that has the nature of a metabolite thereof accumulating in a tumor, the first fluorescent dye and the second fluorescent dye placed in the body of a patient;

emitting, toward the patient, a white light;

selectively causing first fluorescent light that is emitted by the first fluorescent dye, second fluorescent light that is emitted by the second fluorescent dye, and visible light that is reflected by the patient, to be incident into the plurality of imaging elements, by a filter; and displaying a first fluorescent image, a second fluorescent image, and a visible image on a displaying portion based on the first fluorescent light, the second fluorescent light, and the visible light captured by a plurality of imaging elements through the filter, wherein the displaying the second fluorescent image includes generating the second fluorescent image through taking a difference between the light of wavelengths corresponding to the second fluorescent light when a light source, that emits the light of the second wavelength towards the patient, is ON and the light of wavelengths corresponding to the second fluorescent light when the light source is OFF.

9. An imaging method as set forth in claim 8, wherein:

the first fluorescent dye is indocyanine green, or the second fluorescent dye is 5-aminolevulinic acid.

10. An imaging device wherein a first fluorescent dye that emits light through being illuminated with excitation radiation, and a second fluorescent dye that emits light through being illuminated with excitation radiation, and that has the nature of a metabolite thereof accumulating in a tumor, are adapted to be placed in the body of a patient, and fluorescent light from the first fluorescent dye and fluorescent light from the second fluorescent dye are imaged, comprising:

a first light source configured to emit, toward the patient, light of a first wavelength for stimulating the first fluorescent dye;

a second light source configured to emit, toward the patient, light of a second wavelength, different from the first wavelength, for stimulating the second fluorescent dye;

a third light source configured to emit, toward the patient, a white light;

a plurality of imaging elements;

a filter configured to selectively cause first fluorescent light that is emitted by the first fluorescent dye, second fluorescent light that is emitted by the second fluorescent dye, and visible light that is reflected by the patient, to be incident into the plurality of imaging elements; and an image processing portion configured to display a first fluorescent image, a second fluorescent image, and a visible image on a displaying portion based on the first fluorescent light, the second fluorescent light, and the visible light captured by the plurality of imaging elements through the filter, wherein the first fluorescent dye, through being illuminated with the excitation radiation, emits infrared radiation as the fluorescent light, and the second fluorescent dye, through illumination with the excitation radiation, emits visible light as the fluorescent light;

the plurality of imaging elements include a first imaging element able to capture visible light, a second imaging element able to capture the second fluorescent light that is emitted by the second fluorescent dye, and a third imaging element able to capture the first fluorescent light emitted by the first fluorescent dye;

the filter includes a half-mirror configured to reflect a portion of the visible light, reflected by the patient, to cause the visible light to be incident into the first imaging element, and a dichroic mirror configured to pass the first fluorescent light that has passed through the aforementioned half-mirror to cause the first fluorescent light to be incident into the third imaging element, and to reflect the second fluorescent light, which has passed through the aforementioned half-mirror, to cause the second fluorescent light to be incident into the second imaging element;

the image processing portion includes a visible image processing portion configured to perform image processing on the visible light captured by the first imaging element to display the visible light as the visible image on the displaying portion, a second fluorescent image processing portion configured to perform image processing on the second fluorescent light, captured by the second imaging element, to display the second fluorescent light as the second fluorescent image on the displaying portion, and a first fluorescent image processing portion configured to perform image processing on the first fluorescent light, captured by the third imaging element, to display the first fluorescent light as the first fluorescent image on the displaying portion;

the visible image processing portion performs image processing on the visible light reflected from the patient when the third light source is ON to display the visible light as the visible image on the displaying portion;

the second fluorescent image processing portion performs image processing on the second fluorescent light that is emitted by the second fluorescent dye when the second light source is ON, to display the second fluorescent light as the second fluorescent image on the displaying portion; and the first fluorescent image processing portion performs image processing on the first fluorescent light that is emitted by the first fluorescent dye when the first light source is ON, to display the first fluorescent light as the first fluorescent image on the displaying portion.

11. An imaging device wherein a first fluorescent dye that emits light through being illuminated with excitation radiation, and a second fluorescent dye that emits light through being illuminated with excitation radiation, and that has the nature of a metabolite thereof accumulating in a tumor, are adapted to be placed in the body of a patient, and fluorescent light from the first fluorescent dye and fluorescent light from the second fluorescent dye are imaged, comprising:

a first light source configured to emit, toward the patient, light of a first wavelength for stimulating the first fluorescent dye;

a second light source configured to emit, toward the patient, light of a second wavelength, different from the first wavelength, for stimulating the second fluorescent dye;

a third light source configured to emit, toward the patient, a white light;

a plurality of imaging elements;

a filter configured to selectively cause first fluorescent light that is emitted by the first fluorescent dye, second fluorescent light that is emitted by the second fluorescent dye, and visible light that is reflected by the patient, to be incident into the plurality of imaging elements; and an image processing portion configured to display a first fluorescent image, a second fluorescent image, and a visible image on a displaying portion based on the first fluorescent light, the second fluorescent light, and the visible light captured by the plurality of imaging elements through the filter, wherein the first fluorescent dye, through being illuminated with the excitation radiation, emits infrared radiation as the fluorescent light, and the second fluorescent dye, through illumination with the excitation radiation, emits visible light as the fluorescent light;

the plurality of imaging elements include a first imaging element able to capture light of blue wavelengths, a second imaging element able to capture light of green wavelengths, and a third imaging element able to capture light of red wavelengths or longer;

the filter includes a first dichroic mirror configured to reflect light of a blue wavelength, to cause the light of the blue wavelength to be incident into the first imaging element, and a second dichroic mirror configured to pass light of a red wavelength or longer, which has passed through the first dichroic mirror, to cause the light of the red wavelength or longer to be incident into the third imaging element, and to reflect light of a green wavelength, which has passed through the first dichroic mirror, to cause the light of the green wavelength to be incident into the second imaging element;

the image processing portion includes a visible image processing portion configured to perform image processing on the light captured by the first, second, and third imaging element to display the light as the visible image on the displaying portion, a second fluorescent image processing portion configured to perform image processing on the second fluorescent light, captured by the third imaging element, to display the second fluorescent light as the second fluorescent image on the displaying portion, and a first fluorescent image processing portion configured to perform image processing on the first fluorescent light, captured by the second imaging element, to display the first fluorescent light as the first fluorescent image on the displaying portion;

the visible image processing portion performs image processing on the visible light reflected from the patient when the third light source is ON to display the visible light as the visible image on the displaying portion;

the second fluorescent image processing portion performs image processing on the second fluorescent light that is emitted by the second fluorescent dye when the second light source is ON, to display the second fluorescent light as the second fluorescent image on the displaying portion; and the first fluorescent image processing portion performs image processing on the first fluorescent light that is emitted by the first fluorescent dye when the first light source is ON, to display the first fluorescent light as the first fluorescent image on the displaying portion.

* * * * *